US012138486B2

(12) United States Patent
Delinikolas et al.

(10) Patent No.: US 12,138,486 B2
(45) Date of Patent: Nov. 12, 2024

(54) SYSTEM FOR RADIATION THERAPY

(71) Applicant: The University of Strathclyde, Glasgow (GB)

(72) Inventors: Panagiotis Delinikolas, Glasgow (GB); Bernhard Hidding, Glasgow (GB); Fahim Ahmad Habib, Glasgow (GB)

(73) Assignee: University of Strathclyde, Glasgow (GB)

( * ) Notice: Subject to any disclaimer, the term of this patent is extended or adjusted under 35 U.S.C. 154(b) by 299 days.

(21) Appl. No.: 17/762,304

(22) PCT Filed: Sep. 25, 2020

(86) PCT No.: PCT/EP2020/076936
§ 371 (c)(1),
(2) Date: Mar. 21, 2022

(87) PCT Pub. No.: WO2021/058756
PCT Pub. Date: Apr. 1, 2021

(65) Prior Publication Data
US 2022/0331610 A1 Oct. 20, 2022

(30) Foreign Application Priority Data

Sep. 25, 2019 (GR) .............................. 20190100414
Oct. 28, 2019 (GB) ..................................... 1915586

(51) Int. Cl.
*A61N 5/10* (2006.01)
*H05H 1/54* (2006.01)
(52) U.S. Cl.
CPC .............. *A61N 5/1077* (2013.01); *H05H 1/54* (2013.01); *A61N 2005/1087* (2013.01); *H05H 2245/34* (2021.05); *H05H 2277/11* (2013.01)
(58) Field of Classification Search
None
See application file for complete search history.

(56) References Cited

U.S. PATENT DOCUMENTS 9,168,392 B1 * 10/2015 Balakin ................ A61N 5/1081
11,523,489 B2 * 12/2022 Zhu ........................ H05G 2/003
(Continued)

FOREIGN PATENT DOCUMENTS

GB          2587437 A   *  3/2021   ........... A61N 5/1077
JP       2017168275 A       9/2017
(Continued)

OTHER PUBLICATIONS

International Search Report and Written Opinion Application No. PCT/EP2020/076936, dated Jan. 13, 2021, consists of 13 pages.
(Continued)

*Primary Examiner* — Srinivas Sathiraju
(74) *Attorney, Agent, or Firm* — Patterson + Sheridan, LLP

(57) ABSTRACT

A medical system for providing radiotherapy is disclosed. The system comprises a particle accelerator configured to produce a radiation beam and irradiate at least a part of a subject with the radiation beam. The particle accelerator comprises a plasma zone comprising or configured to receive a plasma, and at least one beam source configured to provide an excitation beam along an axis through the plasma zone. The medical system is configured to provide a plurality of charged particles in the plasma in a region that propagates through the plasma zone behind the excitation beam such that the plurality of charged particles are accelerated to produce a radiation beam comprising the plurality of charged particles with a broadband energy distribution, wherein: at least part or all of the energy distribution of the radiation beam is substantially exponential or power-law; the radiation beam delivers 75% or more of a dose of the charged particles at and below 2 g/cm$^2$; and/or the energy beam has an energy or energy distribution in the range from 10 eV to 10 MeV.

20 Claims, 6 Drawing Sheets

Bremsstrahlung+high energy electrons contamination less than 0.1%

Deposition after 2gr/cm$^2$ less than 5%

(56) References Cited

U.S. PATENT DOCUMENTS

| | | | | |
|---|---|---|---|---|
| 11,524,179 | B2* | 12/2022 | Dunaevsky | A61N 5/1077 |
| 11,557,453 | B2* | 1/2023 | Al-Sadah | H01J 35/112 |
| 11,752,360 | B2* | 9/2023 | Tiao | A61N 5/1014 |
| | | | | 600/3 |
| 2012/0080618 | A1 | 4/2012 | Clayton et al. | |
| 2014/0031594 | A1* | 1/2014 | Sawant | C07C 201/08 |
| | | | | 422/187 |
| 2014/0131594 | A1 | 5/2014 | Hidding et al. | |
| 2015/0273242 | A1* | 10/2015 | Balakin | H05H 13/04 |
| | | | | 600/1 |
| 2015/0343238 | A1* | 12/2015 | Balakin | A61N 5/10 |
| | | | | 600/1 |
| 2015/0352374 | A1* | 12/2015 | Gattiker | A61N 5/1031 |
| | | | | 703/2 |
| 2015/0360057 | A1* | 12/2015 | Balakin | A61N 5/1067 |
| | | | | 600/1 |
| 2016/0199667 | A1* | 7/2016 | Flynn | G21K 1/04 |
| | | | | 600/1 |
| 2016/0250501 | A1* | 9/2016 | Balakin | A61B 6/025 |
| | | | | 600/1 |
| 2016/0250503 | A1* | 9/2016 | Balakin | A61N 5/1067 |
| | | | | 600/1 |
| 2016/0256709 | A1* | 9/2016 | Robar | A61B 6/5217 |
| 2017/0332468 | A1* | 11/2017 | Milchberg | H05G 2/008 |
| 2020/0108278 | A1* | 4/2020 | Friedman | G01T 1/20188 |
| 2020/0338364 | A1* | 10/2020 | Swerdloff | A61N 5/1037 |
| 2020/0376296 | A1* | 12/2020 | Balakin | A61N 5/1043 |
| 2021/0046330 | A1* | 2/2021 | Kleven | A61N 5/1068 |
| 2021/0370101 | A1* | 12/2021 | Michaud | A61N 5/1044 |
| 2021/0387022 | A1* | 12/2021 | Raymond | G21K 1/10 |
| 2022/0032088 | A1* | 2/2022 | Friedman | A61N 5/1045 |
| 2022/0331610 | A1* | 10/2022 | Delinikolas | H05H 1/54 |
| 2023/0372736 | A1* | 11/2023 | Duan | A61N 5/1031 |

FOREIGN PATENT DOCUMENTS

| | | | | |
|---|---|---|---|---|
| WO | | 2018069670 A1 | 4/2018 | |
| WO | WO-2021058756 A1 * | | 4/2021 | A61N 5/1077 |

OTHER PUBLICATIONS

T. Königstein et al: "Design considerations for the use of laser-plasma accelerator for advanced space radiation studies", Journal of Plasma Physics, vol. 78, No. 04, Feb. 16, 2012, pp. 383-391.

Yasuhiro Kuramitsu et al: "On the universality of nonthermal electron acceleration due to quasi-turbulent wakefields", High Energy Density Physics, Elsevier, Amsterdam, NL, vol. 8, No. 3, Mar. 29, 2012, pp. 266-270.

Kainz K K et al: "Dose properties of a laser accelerated electron beam and prospects for clinical application" Medical Physics, AIP, Melville, NY US. vol. 31, No. 7, Jul. 1, 2004, pp. 2053-2067.

GB Search Report Application No. GB1915586.0, dated Jun. 18, 2020, consists of 5 pages.

Nuclear Instruments & Methods in Physics Research A, vol. 636, 2011, B Hidding et al.,., "Laser-plasma-accelerators—A novel, versatile tool for space radiation studies", pp. 31-40.

International Preliminary Report on Patentability Application No. PCT/EP2020/076936, dated Mar. 15, 2022, consists of 10 pages.

* cited by examiner

SYSTEM FOR RADIATION THERAPY

FIELD

This disclosure relates to a system for providing radiotherapy and associated methods of treatment of skin conditions, by using a radiation beam having a broadband energy distribution, such as an energy distribution that is substantially exponential or power-law.

BACKGROUND

Radiation therapy, or radiotherapy, is a form of medical treatment involving the provision of high-energy radiation to selected tissue, e.g. to a tumour.

The high energy radiation may comprise high-energy particles, such as gamma rays, x-rays, protons or electrons. Such radiation may damage or destroy cancer cells, for example.

Different forms of radiation, both in terms of the particles and associated characteristics of energy deposition profiles within the body, may be selected or adapted depending upon a treatment required. For example, x-ray photons or high energy electrons (e.g. 150 MeV) or protons (e.g. 200 MeV) may be used to treat tumours that are located deep inside of a patient body. In contrast, electrons of comparably low energy (e.g. few MeV) may be used to treat tumours that are on, or close to, the skin of a patient, e.g. superficial cancers. This is because lower energy electron beams are characterized in that they do not propagate deep into the tissue of a patient. For example, electron beams may be suited to treatment of disease within a few cm of the skin surface, such as cancers of the skin and lips, or upper respiratory and digestive tracts. The higher the kinetic energy of a particle, the deeper it will statistically penetrate into the body.

However, charged particle beams may come from radioactive substances which has safety issues, or may typically be produced by particle accelerator systems such as linear, metallic cavity based accelerators or cyclotrons, and then need to be transported towards the patient via charged particle beamlines, which typically make use of magnets, dipoles and other components to transport the particle beam. At high particle energies, these accelerators and transport systems are bulky and costly and have challenging maneuverability, and at low particle energies the generation and transport of beams is limited by the repulsive space charge of the particles, which is more deleterious at low energies and beam currents.

Existing medical instruments may employ electron guns with linear accelerators (LINAC) to generate essentially mono-energetic electron beams for use in radiotherapy, mainly as a source to indirectly generate photon beams for x-ray radiation therapy via bremsstrahlung. The energy of the mono-energetic electron beams may be selected with above mentioned constraints as regards minimum electron energies, and e.g. an energy of approximately 6 MeV is typically used to produce bremsstrahlung for x-ray radiation therapy for deep seated tumours. The use of monoenergetic electron beams at energies around 150 MeV for direct radiation therapy of deep seated tumours is under investigation. Skin cancer treatment directly by electron beams uses few-MeV, monoenergetic electron beams produced by accelerator systems similar to those which are converted into x-ray beams for deep seated tumour treatment. However, to deliver a significant dose close to the surface and to avoid too high damage of surrounding healthy tissue, such monoenergetic electron beams may require significant transversal dose distribution by oblique irradiation, and multiple angles, and treatment times in order to confine the treatment to the target in-depth distributions.

It is an object of at least one embodiment of at least one aspect of the present disclosure to seek to obviate or at least mitigate one or more of the aforementioned problems.

SUMMARY

Various aspects of the present invention are defined in the independent claims. Some preferred features are defined in the dependent claims.

According to a first aspect of the present disclosure, there is provided a medical system for providing radiotherapy, the medical system comprising a particle accelerator configured to produce a radiation beam for irradiating at least a part of a subject. The particle accelerator comprises a plasma zone that comprise a plasma or is configured to accommodate or contain a plasma, and at least one beam source configured to provide an excitation beam, e.g. along an axis, through the plasma zone.

The medical system may be configured to provide a plurality of charged particles in the plasma in a region that propagates through the plasma zone behind the excitation beam such that the plurality of charged particles are accelerated to produce the radiation beam comprising or with the plurality of charged particles, the radiation beam having a broadband energy distribution, such as an energy distribution that is substantially exponential or power-law. The number or flux of charged particles in the radiation beam may decrease with increasing energy, e.g. may decrease exponentially or according to a power law, over at least part or all of the energy range of the charged particles.

The medical system may be configured to provide a plurality of charged particles in the plasma in a region that propagates through the plasma zone behind the excitation beam such that the plurality of charged particles are accelerated to produce a radiation beam comprising the plurality of charged particles that may have a broadband energy distribution and may give rise to a dose-depth profile that delivers 75% or more, 95% or more, 99% or more or substantially all of a dose of the charged particles in the subject at 2 $g/cm^2$ or less and/or has an energy or energy distribution in the range from 10 eV to 10 MeV, e.g. from 500 keV to 10 MeV, such as in the range from 2 MeV to 10 MeV.

Advantageously, accelerated charged particles having an energy distribution that is substantially exponential or power-law may be used to treat skin conditions with minimal damage to surrounding tissue. For example, existing methods of treating skin conditions with electrons typically use irradiation with beams of few-MeV scale, mono-energetic electrons with a low (i.e. oblique) angle between the skin and the electron-beam. This avoids the electrons to penetrate deep into the tissue in the normal direction and, by repeatedly changing the angle during the treatment sessions, distributes the dose delivered into the surrounding healthy tissue such that the maximum dose received in the healthy issue is reduced and repair mechanisms of the body can prevent cell death within healthy tissue. However, monoenergetic electrons of few MeV energies, as obtainable from existing LINAC technology, have their peak dose deposition not at the surface, where the skin cancer is located, but deeper inside the body, which means for typical surface cancer volumes substantial particle beam energy and damage may be delivered into the surrounding tissue despite the described efforts of multiple angle irradiation and connected extended treatment times.

The methods described herein may use accelerated charged particles, such as electrons, with a broadband energy profile, such as a substantially exponential or power-law energy distribution, which may prevent or reduce deposition of accelerated charged particles into unwanted areas, e.g. deep penetration of the accelerated charged particles into the tissue.

Advantageously, this allows the accelerated charged particles to be incident on the skin at a less oblique angle (e.g. normal to the surface), which makes it easier to aim at the treatment area, which in turn reduces the risk of damage to skin surrounding the treatment area. The incidence of accelerated charged particles upon the skin with a less oblique angle of incidence may limit a transverse dose distribution of the accelerated charged particles. Preferably, the radiation beam may be substantially perpendicular to the surface of the skin. The radiation beam may be within ±20°, e.g. ±10° or ±5° of the normal direction, i.e. the perpendicular direction to the surface of the skin.

The medical system may be for beam radiation therapy.

The system may be provided with an energy distribution and/or dose control system for adjusting and/or selecting, e.g. dynamically selecting, a part or subset of the exponential or power law energy profile and/or for adjusting or selecting, e.g. dynamically selecting, a dose depth profile or energy distribution of the radiation beam. In this way, the energy or energy profile of the radiation beam and/or charged particles emitted by the system may be dynamically variable and/or selectable.

At least one parameter of the excitation beam and/or the plasma may be selected or varied to determine characteristics of the radiation beam. Beneficially, different energy distributions of the radiation beam may be selected by varying one or more parameters of the excitation beam focused upon the plasma and/or of the plasma itself. In this way the excitation beam (e.g. a laser beam or particle beam) and/or the plasma parameters (such as plasma density and/or shape) may be controllable in order to select the energies or energy distribution of the charged particles and/or radiation beam that is emitted. In this case, the energy distribution and/or dose control system may comprise a controller for controlling the at last one beam source to control the one or more parameters of the excitation beam so as to select or vary the energy distribution and/or dose-depth profile of the radiation beam.

The at least one parameter of the excitation beam may optionally comprise one or more of: energy, duration, focus, beam size, beam wavelength, beam shape, and/or beam power density, and/or the like. The at least one parameter of the plasma may optionally comprise one or more of: plasma density, plasma density profile, species, shape and/or the like.

The system may comprise a selection collimator. The selection collimator may be configured to select a portion, e.g. a part or subset, of the radiation beam and/or charged particles, e.g. to select a portion, part or subset of the energy or energy distribution or dose-depth profile of the radiation beam and/or charged particles that are emitted from the system. The selection collimator may be configured to select part of the exponential or power law energy distribution of the charged particles. The selection collimator may be configured to select the energy or energy distribution or dose-depth profile of the radiation beam and/or charged particles. This may contrast with systems that use a collimator to select the beam area on the subject. The system may be provided with means for adjusting which part of the radiation beam or which of the charged particles pass through the selection collimator. The means for adjusting may comprise one, two or more magnets or pairs of magnets, such as electromagnets, opposing quadrupoles or dipoles, and/or the like. In this way, the energies or energy distribution of the charged particles and/or radiation beam that is emitted may be controlled, e.g. selected from the exponential or power law energy distribution of the charged particles. In this case, the energy distribution and/or dose control system may comprise the selection collimator.

The system may comprise a focusing system, which may be configured to focus the radiation beam, e.g. to vary or select the charged particles that are incident on the subject from the plurality of charged particles dependent on the energy of the charged particles, e.g. such that a portion, part or subset of the charged particles representing a part, portion or subset of the energy distribution are incident on the subject. In this way, the range of the energy distribution or dose-depth profile may be selected or dynamically adjusted.

The focusing system may comprise focusing optics. The focusing system may comprise one or more pairs of opposing dipoles, one or more pairs of magnets, which may be electromagnets, and/or the like. The one or more magnets of the focusing system may be or comprise dipole or quadrupole magnets, which may be arranged in opposing pairs. The focusing system may comprise a plasma lens or the like. The one or more magnets may be configured to steer and/or shape the radiation beam. The magnet(s) may be or comprise a bending magnet, which may be or comprise a dipole. The one or more magnets may be configured to collimate, focus and/or restrict the radiation beam to a predefined area. The energy distribution and/or dose control system may comprise the focusing system.

The focusing system may be configured to adjust the energy or energy distribution of, or the dose applied by, the charged particles and/or radiation beam, e.g. by scanning, selecting or varying the part of the exponential or power law energy distribution of the charged particles that is focused onto a target or onto the selection collimator.

Although various mechanisms for controlling the energy or energy distribution of, or the dose delivered by, the charged particles or radiation beam are identified above, it will be appreciated that some or all of the above, e.g. the control of the parameters of the excitation beam (e.g. laser), the use of the selection collimator and the use of the focusing system may be used alone or in combination. Other techniques may potentially be used instead of or in addition to any or all of those identified above.

The plurality of charged particles may comprise electrons. The accelerated charged particles may be electrons, e.g. the radiation beam may be an electron beam. Beneficially, an electron beam does not penetrate deep into deep into tissue, making the system particularly suited to treating skin conditions, such as tumours located near a skin surface. Systems described herein may provide an electron beam having a broadband energy distribution in which the number or flux of charged particles forming the radiation beam decreases with increasing energy, e.g. with an exponential or power-law energy profile, which may allow for better control of electron penetration depth without undue spread of the radiation dose beyond a desired region.

The at least one beam source may be or comprise a laser, radiation beam generator or charged particle generator such as an electron beam generator, proton beam generator, positron beam generator, muon beam generator, ion beam generator, or the like. The at least one beam source may be or comprise a linear accelerator (LINAC). The at least one beam source may be configured to produce a monoenergetic charged particle beam. The at least one beam source may comprise a laser. The excitation beam may be a charged particle beam such as an electron beam or proton beam or positron beam. The excitation beam may be or comprise a laser beam.

The particle accelerator may be, or may comprise, a wakefield accelerator, such as a plasma wakefield accelerator (PWFA) or a laser wakefield accelerator (LWFA). Particles may be accelerated by the LINAC (Linear Accelerator) before subsequently being accelerated by the wakefield accelerator. Alternatively or additionally, particles may be accelerated by means of wakefield acceleration before subsequently being accelerated by a LINAC. The system may comprise the LINAC.

The plasma zone may be or may be comprised in a plasma chamber, which may be located in a low pressure chamber, e.g. a partial vacuum chamber.

The system may comprise one or more plasma generators. At least one of the plasma generators may comprise an ionization device, such as a laser, heater, electromagnetic coil and/or the like, which may be configured to form the plasma in a gas or plasma source and/or in the plasma zone. Alternatively, the plasma may be formed by the excitation beam.

At least one of the plasma generators may comprise a plasma or gas source, such as a gas jet, which may be configured to provide the plasma in the plasma zone. That is, the gas jet may comprise an apparatus for injecting a jet of gas, i.e. a nozzle. The jet of gas may be injected into a vacuum, such as a vacuum in the plasma zone. The gas injected by the gas jet may be ionisable by the ionization device and/or the excitation beam in order to form the plasma. The use of a gas jet to form the plasma may allow for a faster repetition rate, or a continuous gas stream. The beam source may be operable at repetition rates in the order of kHz or higher.

A pulse rate of the at least one beam source (e.g. the one or more lasers) may be selectable, configurable and/or re-configurable.

The particle accelerator may comprise a target material and the plasma generator may comprise a first laser configured to focus a first laser beam onto the target material. In example embodiments, the target material may be or comprise hydrogen or other elements, atoms or molecules with low ionization energies, such as alkali metals and/or a noble gas such as helium or a higher atomic number element, such as krypton. The target material may either be solid, liquid or gaseous or may already be in a plasma state.

At least one parameter of the target material may be selected or varied to determine characteristics of the radiation beam.

The at least one parameter of the target material may comprise: physical state, thickness, density, material, composition, structure, temperature and shape.

A plasma may be created by action of the ionization device and/or the beam source that creates the excitation beam on the target material.

The at least one beam source may be configured to generate a non-uniform electric field that propagates in a direction along the axis through the plasma, with the excitation beam. The non-uniform electric field may be created by the separation of the electrons and ions of the plasma.

Different particles in the plurality of charged particles may experience a different acceleration due to the non-uniform electric field. The non-uniform electric field may be configured to accelerate a plurality of charged particles, such as the bunch of charged particles, with large time-correlated energy spread. The non-uniform electric field may result in non-uniform acceleration of charged particles.

The non-uniform electric field may be separate to any electric field which may create and/or maintain the plasma, such as an electromagnetic field that creates and/or maintains the plasma.

The non-uniform electric field may comprise at least one indicative feature. The indicative feature may be or comprise one or more of: a peak, trough, valley, local minima or maxima, a region with an electric field constant within a threshold value, or the like. The at least one indicative feature may propagate through the plasma.

The indicative feature, e.g. trough in the electric field, may be or may be comprised in the region that propagates behind the excitation beam. The system may be configured to provide the plurality of charged particles in the region into the part of the non-uniform electric field that defines the indicative feature, e.g. trough in the electric field.

The energy distribution of the plurality of charged particles after acceleration through the plasma may be determined by simulation. For example the energy distribution may be determined or approximated by solving the plasma wave Poisson equation, optionally in 1D. This may allow the non-uniform electric field required to produce a particular energy distribution of to be determined.

The simulation may use the desired energy distribution of the plurality of charged particles as a boundary condition. The simulation may use the initial properties, such as spatial distribution, total charge, location, mass and species of the plurality of charged particles as input parameters. The simulation may use the properties of the plasma, such as species and plasma density as input parameters. The simulation may use plasma wave properties, such as wavelength, amplitude and/or propagation speed, as input parameters. The simulation may use properties of the beam source, e.g. of the laser beam or driving particle beam which is used to create the plasma wave, as input parameters, such as laser beam intensity, repetition or pulse rate, wavelength, spot size, energy and power; and/or driving particle beam species, charge, energy distribution, spatial distribution, emittance and/or evolution. Plasma wave wavelength, amplitude and strength and/or propagation speed may be calculated from the laser beam or driving particle beam properties.

The 1D Poisson equation for laser driven plasma wakefield accelerator is:

$$k_p^{-2}\frac{\partial^2 \phi}{\partial \xi^2} = \frac{n_w}{n_0} + \frac{(1+a_0^2)}{2(1+\phi)^2} - \frac{1}{2}$$

The 1D Poisson equation for the wake in a particle beam driven plasma wakefield accelerator, is:

$$k_p^{-2}\frac{\partial^2 \varphi}{\partial \xi^2} = \frac{n_{drive}+n_w}{n_0} + \frac{1}{2(1+\varphi)^2} - \frac{1}{2}$$

where $k_p$ is the plasma wavenumber, $\xi=z-v_p t$ is the co-moving coordinate (z is the coordinate in the laboratory frame, $v_p$ is the plasma wake phase velocity and t is the time), $n_{drive}$ is the (non-evolving) electron driver charge density, $n_0$ is the unperturbed plasma density, $n_w$ is the accelerated electron beam charge density, $a_0$ is the normalized laser pulse amplitude corresponding to the laser intensity and $\phi$ is the scaled electrostatic potential. While the above equations respectively describe laser pulse driven plasma waves and electron beam driven plasma waves, similar equations describe plasma waves driven by positively charged particles, e.g. positron or proton beams, where the main difference to the electron beam driven case is a reversed initial plasma electron trajectory due to the positive charge of positrons as well as of protons or ions, and plasma waves driven by longer wavelength laser pulses, where the propagation speed of the driver is given by the laser pulse group velocity.

The plurality of charged particles may comprise a group, bunch, collection, packet or beam of charged particles. The plurality of charged particles may comprise at least one of electrons, positrons, protons, muons and ions.

The plurality of charged particles may be accelerated to high energies, for example relativistic energies, such as in a range from 10 eV up to 10 MeV. The plurality of charged particles may be accelerated over a distance in a range, e.g. from millimetres to centimetres or centimetres to a metre or more. The plurality of charged particles may propagate collinearly with the laser pulse or driver particle beam which creates the plasma wave. As will be described in more detail below, one or more magnets may be used to separate a direction of propagation of the laser pulse or driver particle beam from a direction of propagation of the plurality of charged particles but this is not essential and instead the laser pulse or driver particle beam can be emitted with the plurality of charged particles.

In examples in which the at least one beam source may comprise a laser and/or the plasma is created by excitation of a material by a laser, then the laser may comprise a fibre or thin disc laser. These particular lasers may have efficiency benefits in the present system. As such, the laser may be located remotely from the particle accelerator. Furthermore, the system may be adapted to accommodate movement between the plasma zone and the laser, such as during adjustment of the medical system for targeting the radiation beam at a subject.

The laser may be configured to operate in a pulsed mode.

The laser may be configured to operate at between 1 Hz and 1 MHz. More preferably, the laser may be configured to operate in a pulsed mode at between 1 kHz and 500 kHz.

The beam source may be configured to produce a beam of particles. For example, the system may comprise a thermionic electron source, a field-emission electron source and/or a Schottky electron source. The beam source may comprise an electron gun. The electron gun may be a DC gun. The DC gun may be a pulsed and/or amplitude modulated DC gun. The electron gun may be a RF gun.

The beam of particles produced by the beam source may be an electron beam. The beam of particles produced by the beam source may be an electron beam with a linearly ramped current profile. Advantageously, this may achieve a desirable exponential spectrum. Alternatively, a Gaussian shaped profile may be used. The beam of particles produced by the beam source may be a substantially mono-energetic beam.

The source of charged particles may be adapted to provide the plurality of charged particles in the plasma in the region that propagates through the plasma zone behind the excitation beam.

The source may comprise an accelerator. The source may comprise a LINAC.

A power density of the particle source may be varied, selected or configured to determine and/or define characteristics of the radiation beam.

The radiation beam may have an energy distribution that is substantially exponential or power-law, e.g. over at least part of a range from 10 eV to 50 MeV. More preferably, the energy distribution may be substantially exponential or power-law over at least part of a range from 100 keV to 10 MeV.

The radiation beam may produce, e.g. may be selected or configured to produce, a Bremsstrahlung background of typically less than 1% of an entry dose when incident upon a subject, e.g. skin of a subject. Advantageously, a Bremsstrahlung background of less than 1% and/or with low, e.g. sub-keV, Bremsstrahlung photon energies due to the low incident electron energies may result in significantly less damage to surrounding tissue than the use of conventional mono-energetic beams obliquely delivered with a low angle of incidence.

The system may further comprise a treatment head and optionally a support or frame. The support or frame may support the treatment head. The support or frame may be configured such that the treatment head is rotatable about a subject. The treatment head may be configurable to output the radiation beam. One or more of the plasma zone, the plasma generator and optionally the selection collimator and/or the focusing optics may be comprised in the treatment head. The at least one beam source may be remote from the treatment head. The system may comprise a pathway for transporting the excitation beam from the beam source to the plasma zone. In examples where the at least one beam source comprises a laser and the excitation beam is a laser beam, then the pathway may comprise at least one optical fibre or optical fibre bundle and/or the pathway is at least partly defined by one or more, e.g. a series of, mirrors and/or other optical elements, configured to convey the excitation beam from the remote beam source to the plasma zone in the treatment head. This pathway arrangement may be configured or configurable to guide the excitation beam around corners and/through one or more changes in direction. The treatment head, where the radiation beam is produced from the plasma, is preferably located or locatable in the vicinity of, proximate or adjacent the skin surface to be treated, in use. Beneficially, in this way, the electron beam may generated in the vicinity of the area of the body to be treated, e.g. in the vicinity of, proximate or adjacent the skin surface. The beam source, however, can be provided remotely from the plasma zone used to generate the electron beam, e.g. the beam source may be provided in a separate base unit or on a fixed part of the support or frame. The treatment head may be movable relative to the beam source. The pathway may be flexible or conformable, e.g. the at least one optical fibre or optical fibre bundle may be sufficiently flexible or conformable to accommodate the relative motion of the treatment head and beam source. In this way, a relatively compact and low bulk system may be provided that does not require sizable waveguides, e-beam steering magnets or a large gantry that is sufficiently strong to carry the beam source or to move it during treatment that otherwise would make the system very bulky, expensive and cumbersome.

The system may further comprise a supporting track. The track may support the treatment head. The treatment head may be configurable to be moved on the track to rotate the treatment head around a subject. The treatment head may be configurable to output the radiation beam.

The system may further comprise a moveable treatment platform or couch for supporting a subject. The treatment platform or couch may be configurable to be moved relative to a treatment head configurable to output the radiation beam;

The system may further comprise one of more targeting collimators. The targeting collimator may comprise a multi leaf collimator. The targeting collimator may be adapted to block or shape the radiation beam. For example, the targeting collimator(s) may shape the radiation beam to a particular shape such as a shape of a tumour. In this regard, the targeting collimators may be different and/or in addition to the selection collimators. That is, the one or more targeting collimators may control the size and shape of the radiation beam on the subject. The one or more selection collimators may select a portion or part of the plurality of charged particles that form the radiation beam in order to select or define the energy distribution, e.g. the range of energy distribution, of the charged particles in the radiation beam.

The subject may be a patient.

According to a second aspect of the present disclosure, there is provided a method of treating a skin condition of a subject, the method comprising: providing a plasma zone containing or accommodating a plasma; providing an excitation beam, e.g. along an axis, through the plasma zone.

The method may comprise providing the excitation beam such that a plurality of charged particles provided in the plasma in a region that propagates through the plasma zone behind the excitation beam are accelerated to produce a radiation beam comprising the plurality of charged particles with broadband energy distribution, e.g. an energy distribution that is substantially exponential or power-law; and irradiating a subject with the radiation beam. The number or flux of charged particles in the radiation beam may decrease with increasing energy, e.g. may decrease exponentially or according to a power law over at least part or all of the energy range of the charged particles.

The method may comprise providing a plurality of charged particles in the plasma in a region that propagates through the plasma zone behind the excitation beam such that the plurality of charged particles are accelerated to produce a radiation beam comprising the plurality of charged particles, wherein the radiation beam may provide a dose-depth profile in which at least 75%, at least 95%, at least 99% or substantially all of a dose provided by the radiation beam is delivered at 3 g/cm², 2 g/cm², 1 g/cm² and below and/or the radiation beam has an energy or energy distribution in the range from 10 eV to 10 MeV, e.g. from 500 keV to 10 MeV, such as in the range from 2 MeV to 10 MeV.

The method may comprise selecting, e.g. dynamically selecting, charged particles representing only part, e.g. a subset, of the exponential to power law energy profile. In this way, the energy or energy profile of the radiation beam and/or charged particles emitted by the system may be dynamically variable and/or selectable.

The method may comprise selecting or varying at least one parameter of the excitation beam to determine, select or vary the energy distribution and/or the dose-depth profile of the radiation beam. The method may comprise selecting or varying different energy distributions of the radiation beam by varying one or more parameters of the excitation beam focused upon the plasma. In this way the excitation beam (e.g. a laser beam or particle beam) may be controllable in order to select the energies or energy distribution of the charged particles and/or radiation beam that is emitted.

The at least one parameter of the excitation beam may comprise: energy, duration, focus, beam size, beam wavelength, beam shape, and/or beam power density, and/or the like.

The method may comprise providing a selection collimator. The method may comprise selecting a portion, e.g. a part or subset, of the radiation beam and/or charged particles, using the selection collimator to select the energy or energy distribution or dose-dose profile of the emitted radiation beam and/or charged particles. The selection collimator may be configured to select part of the broadband and/or exponential or power law energy distribution of the charged particles. The method may comprise selecting an energy or energy distribution or dose of the radiation beam and/or charged particles, e.g. using the selection collimator. The method may comprise adjusting which part of the radiation beam or which of the charged particles pass through the selection collimator, e.g. using one, two or more magnets, such as electromagnets, opposing quadrupoles or dipoles, and/or the like. The method may comprise controlling the energies or energy distribution of the charged particles and/or radiation beam that is emitted by selecting particles from the exponential or power law energy distribution of the charged particles.

The method may comprise providing a focusing system. The method may comprise focusing the radiation beam and/or the plurality of charged particles using the focusing system. The method may comprise selectively and/or dynamically focusing only a part, portion or subset of the beam or plurality of charged particles representing only a part, portion or subset of the energy distribution or dose-depth profile onto the subject. The focusing system may comprise focusing optics. The focusing system may comprise one or more pairs of opposing dipoles, one or more pairs of magnets, and/or the like. The one or more magnets of the focusing system may be or comprise dipole or quadrupole magnets, which may be arranged in opposing pairs. The one or more magnets may be configured to steer and/or shape the radiation beam. The magnet(s) may be or comprise a bending magnet. The one or more magnets may be configured to collimate, focus and/or restrict the radiation beam to a predefined area.

The radiation beam may be produced by a system according to the first aspect.

The method may comprise providing the radiation beam such that an angle of incidence to a normal of a surface of the subject, e.g. a surface of the skin, is substantially 0 degrees. The method may comprise providing the radiation beam at an angle of incidence to a normal of a surface of the subject in a range from ±30 to 0 degrees, or from ±20 to 0 degrees.

The radiation beam incident upon the subject may cover an area in the region of 10 cm×10 cm, or an area with a radius of approximately 10 cm. The radiation beam incident upon the subject may cover a volume in the region of 10 cm×10 cm×10 cm.

The radiation beam incident upon the subject may be shaped using the one or more targeting collimators. Shaping and/or steering of the radiation beam may be achieved by use of magnets, such as electromagnets. The magnets may be configured to focus, or collimate or confine the radiation beam to a predefined area. Alternatively, or additionally, a plasma lens may be used to focus or shape the radiation beam. The radiation beam may be incident upon the entire target, or sequentially or progressively over at least part of the subject, e.g. by using a raster-scan technique or the like.

A profile of the radiation beam may be controlled by means of controlling an energy distribution of the radiation beam. For example, a three-dimensional profile, or dosage, of the beam when incident upon a subject may be controlled by adjusting, such as continually adjusting, an energy profile of the radiation beam. As such, an effective depth of penetration of the beam into a subject may be controlled, thus allowing matching or correlation of the radiation beam with a shape and/or depth of a target, such as a shape and/or depth of a target tumour.

A distribution, e.g. an energy distribution, of the radiation beam when incident upon a subject may follow a substantially Gaussian or bell-curve profile.

The skin condition may comprise a tumour.

The method may comprise providing the radiation being to the subject during or immediately after surgery, e.g. to irradiate an area inside of the subject around a region from which a tumour has been removed using surgery before a surgical incision in the subject is closed up. In this case, a low dose in the region of 5 to 10 Gy may be administered. This technique may be particularly beneficial if the tumour site is near organs or other sensitive areas.

According to a third aspect of the present disclosure, there is provided a method of adapting a medical radiotherapy apparatus comprising a LINAC to produce a radiation beam having a broadband energy distribution that is substantially exponential or power-law, the method comprising fitting or retrofitting the medical radiotherapy apparatus with a gas jet or plasma cell. The number or flux of charged particles in the radiation beam may decrease with increasing energy, e.g. may decrease exponentially or according to a power law over at least part or all of the energy range of the charged particles.

A particle beam output of the LINAC may be directed into or through the gas-jet or plasma cell, e.g. to facilitate plasma wakefield acceleration. The LINAC may produce a substantially mono-energetic particle beam. A laser may be focused on the gas jet to form a plasma. The electron beam output of the LINAC may interact with, e.g. excite, the plasma. The electron beam output of the LINAC may be accelerated by plasma wakefield acceleration through the plasma formed from the gas jet or the plasma of the plasma cell.

The method may comprise forming the medical system of the first aspect using the LINAC as the beam source and/or particle source described in relation to the first aspect.

According to a fourth aspect of the present disclosure, there is provided a use of a radiation beam having a broadband energy distribution that is substantially exponential or power-law in the treatment of skin conditions. The number or flux of charged particles in the radiation beam may decrease with increasing energy, e.g. may decrease exponentially or according to a power law over at least part or all of the energy range of the charged particles.

According to a further aspect of the present disclosure, there is provided a method of delivering a radiation therapy treatment plan to a patient using a radiation therapy system. The method may comprise configuring the radiation therapy system to produce a radiation beam having a broadband energy distribution. The energy distribution may be substantially exponential or power-law over at least part or all of the energy distribution. The method may comprise irradiating a subject with the radiation beam. The number or flux of charged particles in the radiation beam may decrease with increasing energy, e.g. may decrease exponentially or according to a power law, over at least part or all of the energy range of the charged particles. The method may comprise configuring the radiation therapy system to produce a radiation beam comprising the plurality of charged particles, the radiation beam may provide a dose-depth profile in which at least 75%, at least 95%, at least 99% or substantially all of a dose provided by the radiation beam is delivered at 3 g/cm$^2$, 2 g/cm$^2$, 1 g/cm$^2$ and below and/or the radiation beam may have an energy or energy distribution in the range from 10 eV to 10 MeV, e.g. from 500 keV to 10 MeV, such as in the range from 2 MeV to 10 MeV. The method may comprise providing the radiation beam using the system of the first aspect and/or the method of the second aspect.

According to a further aspect of the present disclosure, there is provided a method for delivering a radiation beam toward a patient, the method comprising configuring a system according to any of the relevant aspects above to produce a radiation beam having a broadband energy distribution, e.g. that is substantially exponential or power-law law over at least part or all of the energy distribution, and irradiating the patient with radiation beam. The number or flux of charged particles in the radiation beam may decrease with increasing energy, e.g. may decrease exponentially or according to a power law, over at least part or all of the energy range of the charged particles.

According to a further aspect of the present disclosure, there is provided a medical system for providing radiotherapy, the system comprising a particle accelerator configured to produce a radiation beam having a broadband energy distribution, e.g. that is substantially exponential or power-law over at least part or all of the energy distribution, and the system being configurable to irradiate a subject with the radiation beam. The number or flux of charged particles in the radiation beam may decrease with increasing energy, e.g. may decrease exponentially or according to a power law, over at least part or all of the energy range of the charged particles.

It should be understood that the features defined above in accordance with any aspect of the present disclosure or below relating to any specific embodiment of the disclosure may be utilised, either alone or in combination with any other defined feature, in any other aspect or embodiment or to form a further aspect or embodiment of the disclosure.

Furthermore, the present disclosure is intended to cover apparatus configured to perform any feature described herein in relation to a method and/or a method of using or producing, using or manufacturing any apparatus feature described herein.

BRIEF DESCRIPTION OF DRAWINGS

These and other aspects of the present disclosure will now be described, by way of example only, with reference to the accompanying drawings, which:

FIG. 1b illustrates an of operation of the plasma accelerator of FIG. 1a;

FIG. 3 a representation of a medical system for providing radiotherapy, the medical system comprising the plasma accelerator of FIG. 1a;

DETAILED DESCRIPTION OF DRAWINGS

Figure 1A:
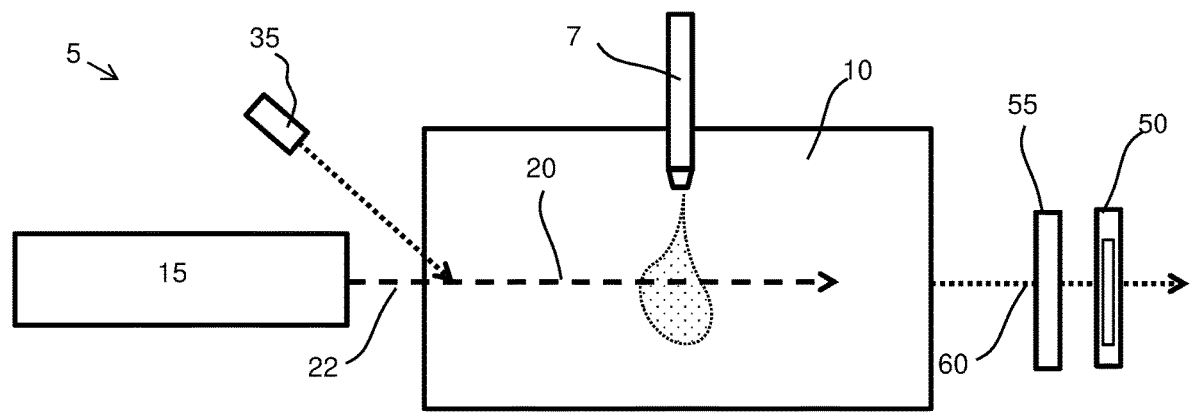
FIG. 1a a plasma accelerator.

Referring firstly to FIG. 1a of the accompanying drawings, there is shown a plasma accelerator 5. The accelerator 5 comprises a plasma zone 10 for containing or otherwise accommodating a plasma. A medium from which the plasma is formed is provided into the plasma zone 10 by a plasma generator 7. In this example, the plasma generator 7 is in the form of a gas jet, which provides a gas that is ionized into plasma by a laser, heater, electromagnetic field generator or the like. The accelerator 5 comprises one or more beam sources 15, such as lasers, electron beam generators, proton beam generators, positron beam generators, ion beam generators, or the like. The beam source 15 is operable to provide an excitation beam 20 along a beam axis 22 through the medium in the chamber 10, thereby forming a plasma wave within the plasma. In this way, the beam sources 15 are operable to excite a longitudinal plasma wave in the medium.

Figure 1B:
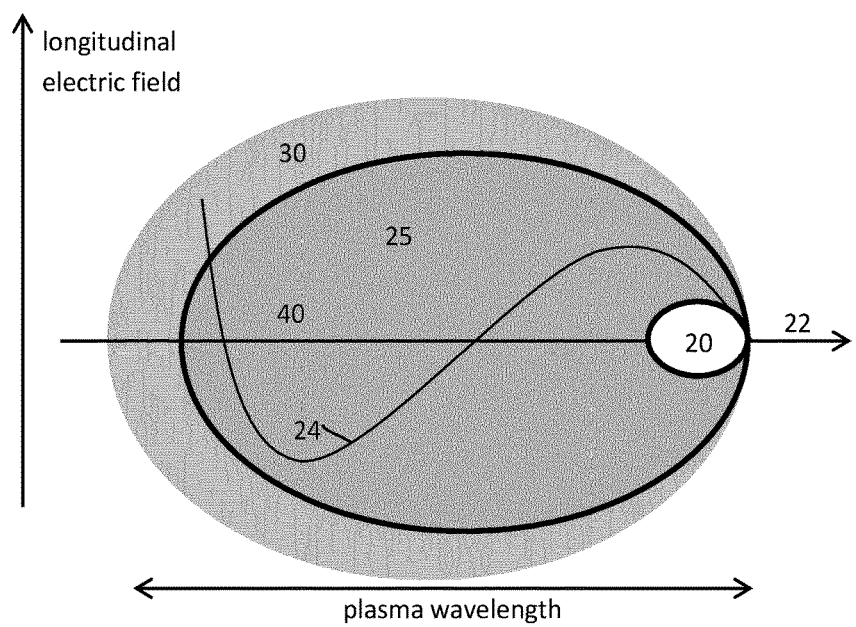

As shown in FIG. 1b, the excitation beam 20 forces a bunch of negatively charged electrons 30 away from the beam axis 22, while the positively charged ions with higher mass remain relatively stationary, resulting in a linear or non-linear plasma wave or in a plasma "blowout" 25. Once the excitation beam 20 has passed, the negatively charged electrons 30 are attracted to the back of the blowout region 25 by the positively charged ions, resulting in excess negative charge at the back of the blowout region 25. The spatial distribution of the negatively charged electrons 30 and the positively charged ions in and around the blowout region 25 results in a non-uniform electric field 24 within the blowout region 25 which propagates through the plasma behind the excitation beam 20. In the example shown in FIG. 1b, the non-uniform electric field 24 defines a trough in the electric field that follows behind the excitation beam 20.

A plurality of charged particles 40 may be added to the plasma or created in the plasma. For example, the plurality of charged particles 40 may be electrons which are created by the ionisation of the plasma by the excitation beam 20. Alternatively, the plurality of charged particles 40 may be added to the plasma by a particle source 35, for example an electron beam which adds electrons to the plasma, or a laser for providing a laser pulse that further ionises the plasma to release free electrons within the plasma. If the plurality of charged particles 40 are negatively charged, such as electrons, and they are located or produced in the trough of the non-uniform electric field 24, near the back of the blowout region 25, they will experience an acceleration due to the non-uniform electric field 24 along the beam axis 22 behind the excitation beam 20. As the electric field 24 is non-uniform, some of the electrons 40 will experience a high force, and hence a larger acceleration, than others of the electrons 40. This will broaden the energy distribution of the electrons 40 which are then emitted as a radiation beam 60 of charged particles (e.g. electrons) having a broadband energy distribution.

Beneficially, the provision of a radiation beam 60 of charged particles with a broadband energy distribution by the plasma accelerator 5 may provide certain benefits when applied to medical applications. For example, the broadband energy distribution of the radiation beam 60 may allow the range of the energy distribution to be dynamically selected or adjusted to suit a given application, e.g. to provide a required dose or penetration depth or dose/depth profile.

There are various mechanism by which such a selection may be provided, which can be used individually or in combination to produce the required energy distribution of charged particles in the radiation beam 60.

One mechanism for selecting or varying the energy distribution of the charged particles in the radiation beam 60 is to control the beam source 15 to control the properties of the excitation beam 22 to thereby vary the properties of the electric field 24 and/or to control the particle source 35 to control the properties of the charged particles 40. For example, properties of the excitation beam 22 such as the energy, duration, degree of focus, beam size, wavelength, beam shape, beam power density and the like can be selected in order to produce the required energy distribution of the charged particles 40 that form the radiation beam 60.

Another mechanism for selecting or varying the energy distribution of the charged particles in the radiation beam 60 involves providing a selection collimator 50. In this way, the energy distribution of the charged particles 40 in the radiation beam 60 can be selected by controlling the radiation beam 60 and selecting a suitable selection collimator 50 such that only the portion of the radiation beam 60 having the charged particles of the required energy distribution (e.g. energy range) is incident on the slit of the selection collimator 50. The charged particles having an energy out with the required energy distribution are blocked. The portion (i.e. subset) of the radiation beam 60 that is incident on the slit of the selection collimator 50 and thereby the energy distribution (e.g. energy range) of the charged particles 40 of the radiation beam 60 can be selected by appropriate selection of the size of the slit, by controlling the energy distribution of charged particles in the radiation beam that is incident on the selection collimator 60 (e.g. by controlling the beam source 15 as described above), by variation of the focusing of the radiation beam 60, by steering of the radiation beam 60 e.g. using magnets or plasma lenses and/or other appropriate techniques.

This use of a selection collimator 50 is different from other systems that provide mono-energetic radiation beams and may use collimators to control the dose area that is incident on the subject. In contrast, the selection collimator 50 can be used in combination with the broadband, e.g. exponential or power law, distribution of charged particle energies to select a required energy range.

Another mechanism for selecting the energy range of the charged particles 40 of the radiation beam 60 comprises use of focusing optics 55, such as one or more plasma lenses and/or magnets such as electromagnets. The magnets may be arranged in opposing pairs and may comprise dipoles or quadrapoles. The focusing optics can be used to focus and/or steer the radiation beam so that a portion (i.e. subset) of the radiation beam 60 having the required energy distribution is incident on the target area of the subject (or the slit of the selection collimator 50).

It will be appreciated that one or more of the above techniques for selecting a desired energy distribution of the charged particles may be used and that combinations of the above mechanisms may interact synergistically in order to provide greater control of the energy distribution of the charged particles of the radiation beam 60.

It will also be appreciated that other suitable techniques for controlling the energy distribution could be used in addition to or instead of the above.

Further variations of the plasma accelerator of FIG. 1a, are described herein. For example, once the electrons 24 have moved part-way through the plasma, and have reached relativistic speeds, a second plurality of charged particles, such as a second group of electrons, may be added to the plasma. The second group of electrons may be added to the plasma by a second particle source (not shown) for example, which may inject electrons into the plasma, or a laser which may be used to further ionize the plasma to form the second group of electrons. The second group of electrons spatially overlap with the electrons 40. The charge of the second group of electrons will affect the non-uniform electric field 24, creating a local distortion in the non-uniform electric field 24. The position and total charge of the second group of electrons will determine the position and size of the local distortion in the non-uniform electric field 24.

As such, the energy distribution of the first plurality of charged particles at the end of the accelerating phase or section of the plasma wave within the plasma may be controlled by controlling at least one of the spatial distribution, total charge, location, mass and species of the second plurality of charged particles, by controlling the timing of adding, injecting or firing the second plurality of charged particles into the plasma, or by controlling the timing of creating the second plurality of charged particles in the plasma. Thus a degree of control over the energy distribution of the first plurality of charged particles at the end of the accelerating phase or section is possible.

Techniques that can be used to achieve this are described in UK Patent Application GB1617173.8, "Plasma Accelerator" and also PCT/GB2017/052942, which are both hereby incorporated by reference in its entirety as if set out in full herein.

Figure 2:
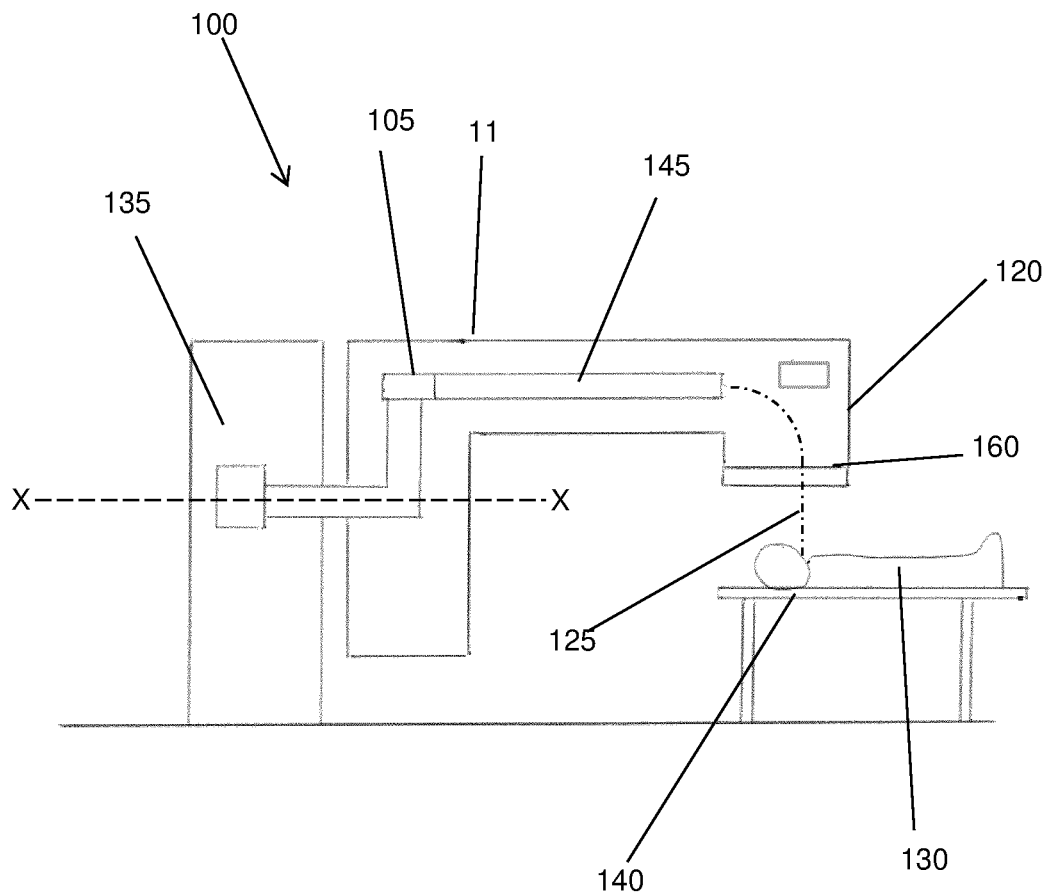
FIG. 2 a representation of a prior art medical system for providing radiotherapy.

Referring to FIG. 2 of the accompanying drawings, there is shown a representation of a prior art medical system, generally denoted 100.

The medical system 100 system comprises a heavy duty gantry 115. The gantry 115 supports a treatment head 120. The treatment head 120 is configurable to output a radiation beam 125. In FIG. 2, the medical system 100 is shown in use, such that the radiation beam 125 is targeted at a subject 130.

The gantry 115 is supported by a stand 135. The gantry 115 is configurable to be rotated about an axis X-X. As such, the treatment head 120 is configurable to be rotated about the subject 130.

The medical system 110 comprises a treatment couch 140 for supporting the subject 130. The treatment couch 140 is configurable to be moved relative to the treatment head 120. As such, the subject 130 may be moved relative to the radiation beam 125.

The medical system 100 comprises a particle accelerator 145. In the prior art medical system, the particle accelerator 145 is an RF Linear Accelerator (LINAC) for producing a monoenergetic electron beam. An electron gun 105 provides a source of electrons to the LINAC 145.

Figure 3:
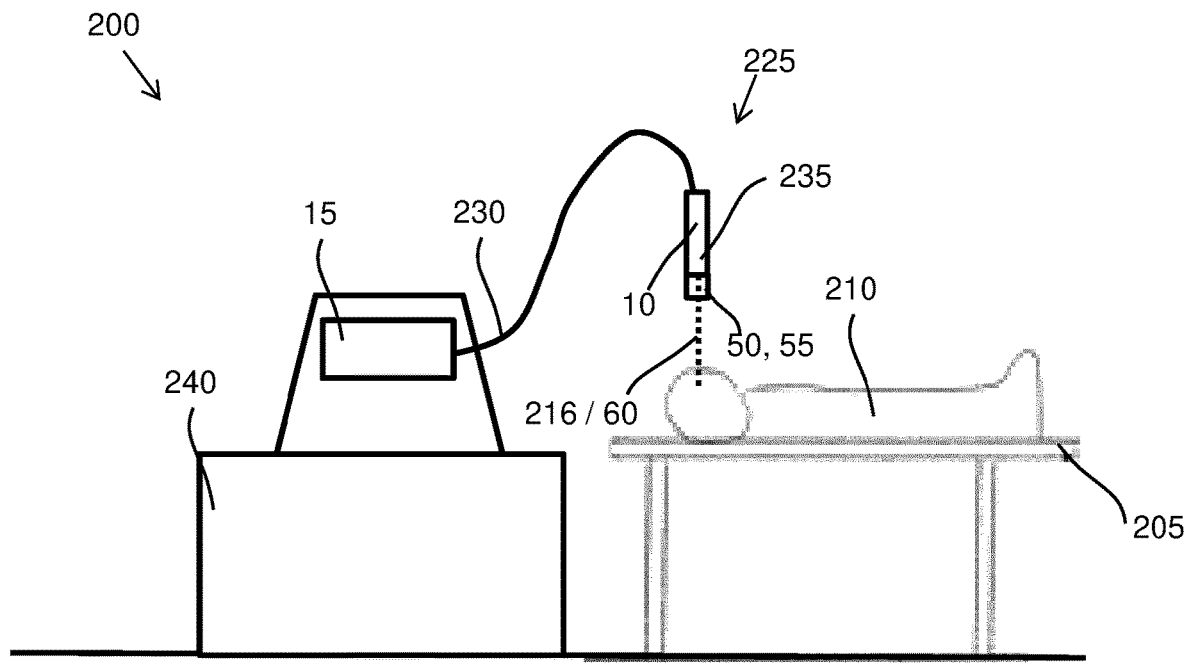

Turning now to FIG. 3 of the accompanying drawings, there is shown a representation of a medical system, generally denoted 200, for providing radiotherapy.

The medical system 200 comprises a treatment couch 205 for supporting a subject 210 to be treated by a radiation beam 215. The medical system 200 comprises a particle accelerator 225. In examples, the particle accelerator 225 is the particle accelerator 10 shown in, and described in relation to, FIG. 1a. That is, the particle accelerator 225 comprises a plasma zone 10 configured to contain or accommodate a plasma supplied using the gas jet 7 and a beam source 15 configured to provide an excitation beam along an axis through the plasma zone 10. As such, the particle accelerator 225 is configured to accelerate particles by means of wakefield acceleration.

Optionally, the particle accelerator 225 further comprises the particle source 35 shown in FIG. 1a that provides a plurality of charged particles to the plasma in a region that propagates through the plasma zone 10 behind the excitation beam such that the plurality of charged particles are accelerated to produce the radiation beam 215 comprising the plurality of charged particles with a broadband energy distribution that is substantially exponential or power-law. Alternatively, no separate particle source need be provided and the beam source 15 may be operable to both produce excess electrons or other charged particles and to create the plasma blowout 25 and consequential non-uniform electric field 24.

The beam source 15 is optionally a laser, e.g. a fibre or other suitable laser. The use of a fibre laser makes it easier for the beam source 15 (laser) to be located remotely from the plasma zone 7. Furthermore, the system may be adapted to accommodate movement between the plasma zone 7 and the beam source (laser) 15, such as during adjustment of the medical system 200 for targeting the radiation beam 225 at the subject 210.

In the example shown, the beam source 15 is provided remotely to the plasma zone 10 and the excitation beam provided to the plasma zone 10 via a suitable pathway 230, e.g. an optical fibre or optical fibre bundle and/or directed using mirrors or other optical elements. In this case, the plasma zone 10 is optionally provided in a treatment head 235 that is movable relative to the subject 210, whilst the beam source 15 (e.g. laser) can be provided in a base unit 240 that is stationary relative to the subject, in use. In this way, the medical system 200 does not comprise a bulky LINAC or the associated wave guides and as such can be made very compact and need not be supported by a bulky and heavy gantry. Instead, the treatment head 235 can be supported on a relative light stand or carrier. This could potentially save not only space, but make the treatment more portable without requiring costly adaptations such as floor reinforcement. It also allows the treatment to be beneficially applied to harder to reach areas and potentially could be uses to provide particle beam treatment during or immediately after surgery, e.g. to irradiate an area inside of the subject 210 around a region from which a tumour has been removed using surgery before a surgical incision in the subject 210 is closed up. In this case, a low dose in the region of 5 to 10 Gy may be administered. This technique may be particularly beneficial if the tumour site is near organs or other sensitive areas.

However, it will be appreciated that other arrangements could be used, e.g. both the beam source 15 and the plasma zone 10 may be provided together in the same unit in order to provide a more compact and robust unit.

As in the example of FIG. 1, the medical system 200 may be configured such that the energy distribution of the charged particles in the radiation beam 215, 20 is adjustable and/or selectable, e.g. dynamically selectable. This may be achieved using, for example, one or more of the mechanisms described above, such as by controlling the beam source 15 and/or particle source 35, using the selection collimator 50, using the focusing optics 55 or any combination thereof. Optionally, components such as the focusing optics 55 and selection collimator 50 can be provided in the treatment head 235 with the plasma zone 10 and plasma generator 7.

In examples, the particle source 35 may comprise a thermionic electron source, a field-emission electron source and/or a Schottky electron source, an electron gun such as a DC gun. The DC gun may be a pulsed and/or amplitude modulated DC gun. The electron gun may be a RF gun. It will be appreciated that such sources may provide charged particles, namely electrons, to the particle accelerator 245.

It will be appreciated that there are different wakefield acceleration techniques that could be used such as laser wakefield acceleration (LWFA) or plasma wakefield acceleration (PWFA).

For example, the beam source 15 (and/or the particle source 35) could be a laser, as described above or could be a particle beam source (such as a LINAC), which could be an electron beam source, a proton beam source, a positron beam source, and/or the like. In this way, for example, the medical system 200 could be provided by retrofitting the treatment head 235 comprising at least the plasma zone 10 and plasma source 7 (e.g. the plasma gas jet) and optionally the selection collimator 50 and/or focusing optics 55, to an existing linear accelerator, which can be used as the beam source 15 and/or as the particle source 35. The plasma zone 10 would receive a mono-energetic charged particle beam that acts as the excitation beam 20 (and/or which may provide the plurality of charged particles 40) from the existing linear accelerator acting as the beam source 15 and/or particle source 35 to produce the broadband charged particle beam 215, 60, that optionally has an exponential or power law energy distribution and whose energy or dose-depth distribution can optionally be selected or adjusted.

In yet a further example, the medical system 200 would not comprise the LINAC, nor an alternative source of the plurality of charged particles. Instead, the plurality of charged particles may be created in the plasma. For example, in an embodiment wherein the plurality of charged particles comprises electrons, the electrons may be created by the further ionisation of ions of the plasma, e.g. using a laser or particle beam generator.

In yet a further example, a radiation beam that is output from the particle accelerator 225 may be input to a further accelerator, such as a LINAC.

Thus, it will be appreciated that a prior art medical system 100, such as that shown in FIG. 2, may be modified by means of installation or retrofitting of the treatment head 235 comprising at least the plasma zone 10, plasma generator 7, and optionally the selection collimator 50 and/or focusing optics 55 to the conventional particle accelerator 245 of the type shown in FIG. 2, to provide an improved medical system for providing radiotherapy.

Figure 4A:
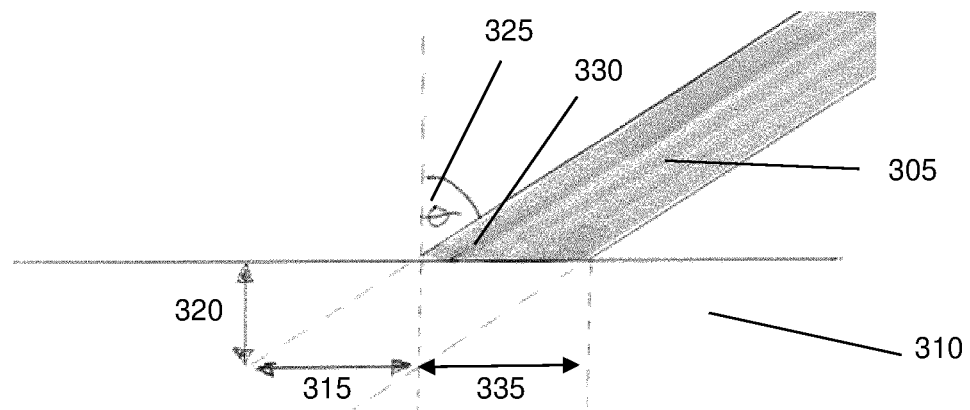
FIG. 4a a schematic diagram showing a radiation beam incident upon a subject according to a conventional medical system.

Turning now to FIG. 4a, there is shown a schematic diagram of a radiation beam 305 incident upon a subject 310 according to a conventional medical system. The radiation beam 305 may be a beam generated by a system 100 such as that shown in FIG. 2. The radiation beam 305 is a beam of substantially mono-energetic electrons. As such, the angle of the beam may be selected to determine a dose depth for the mono-energetic energy of the radiation beam 305.

That is, employing existing techniques for irradiating skin, the beam angle of incidence on the subject determines a dose depth for the given energy level of the substantially mono-energetic radiation beam 305. However, such a radiation beam 305 may provide significant transverse dose distribution 315 due to the required high incidence angles 325 and treatment times in order to confine the treatment to the target in-depth distributions 320. That is, existing methods of treating skin conditions with electrons typically use a low angle 330 between the skin and the high-energy electrons, to prevent the electrons penetrating deep into the tissue. This results in the electrons hitting a large area of skin 335, and a significant transverse dose distribution 315.

Figure 4B:
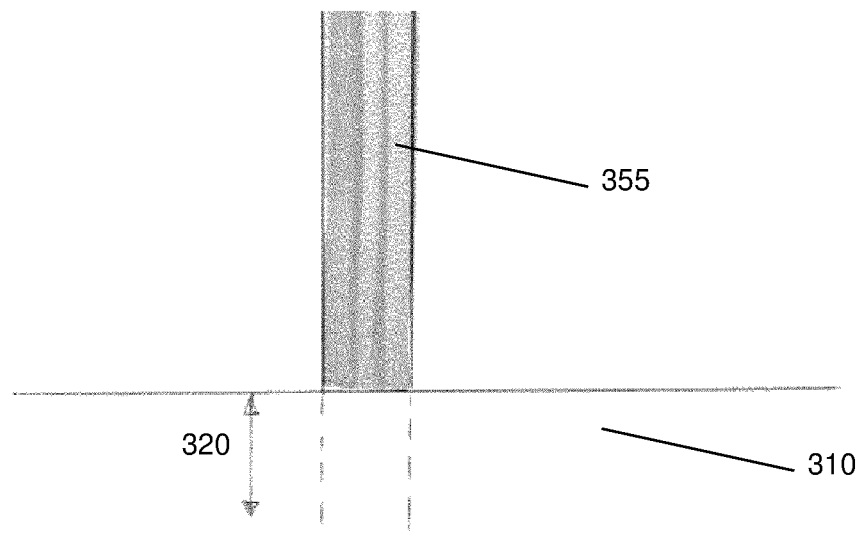
FIG. 4b a schematic diagram showing a radiation beam incident upon a subject according to an example of the present disclosure.

In contrast, the medical system 200 described herein produces a radiation beam 355 comprising a plurality of charged particles with a broadband energy distribution that is substantially exponential or power-law. In this way, the dose of radiation from the radiation beam 355 can be controlled to correspond to a controlled range of depths into the skin. Advantageously, this allows the accelerated charged particles to be incident on the subject 310 at a much higher angle, as shown in FIG. 4b, which makes it easier to aim at the treatment area, which in turn prevents damage to skin surrounding the treatment area of the subject. That is, the incidence of accelerated charged particles upon the subject with a low angle of incidence significantly limits a transverse dose distribution of the accelerated charged particles.

Figure 5:
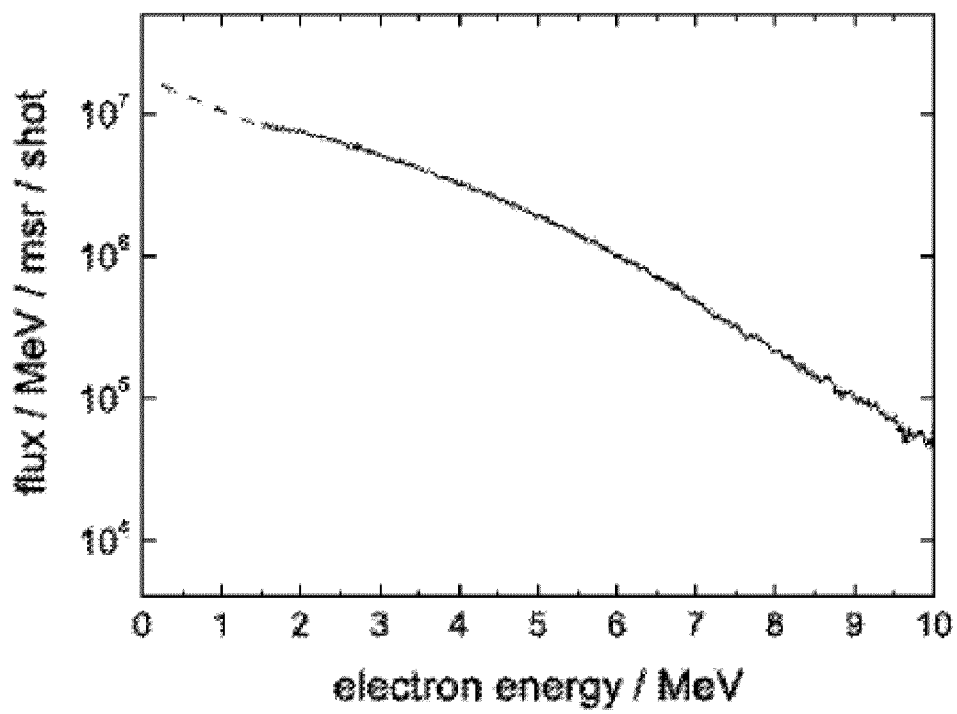
FIG. 5 an experimentally generated electron spectrum producible by laser wakefield acceleration (LWFA)

Turning now to FIG. 5, there is shown an experimentally generated electron spectrum, which is producible with a particle accelerator as used in the medical system 200 of FIG. 3 described herein. Particularly noticeable from FIG. 5 is that the distribution of the energy spectra shown follows a substantially exponential distribution between approximately 2 and 10 MeV. In contrast, while particle accelerators based on existing technology, such as medical RF LINACs (as exemplified in FIG. 2) do not generate particle energy spectra that follow the exponential distribution and instead give substantially mono-energetic distributions, FIG. 5 depicts an example of plasma accelerator generated electron spectrum with a broadband exponential energy distribution. Notably, the exponential spectrum means that most of the electrons are of low energy, therefore have comparably low penetration depths when incident upon a subject.

Figure 6:
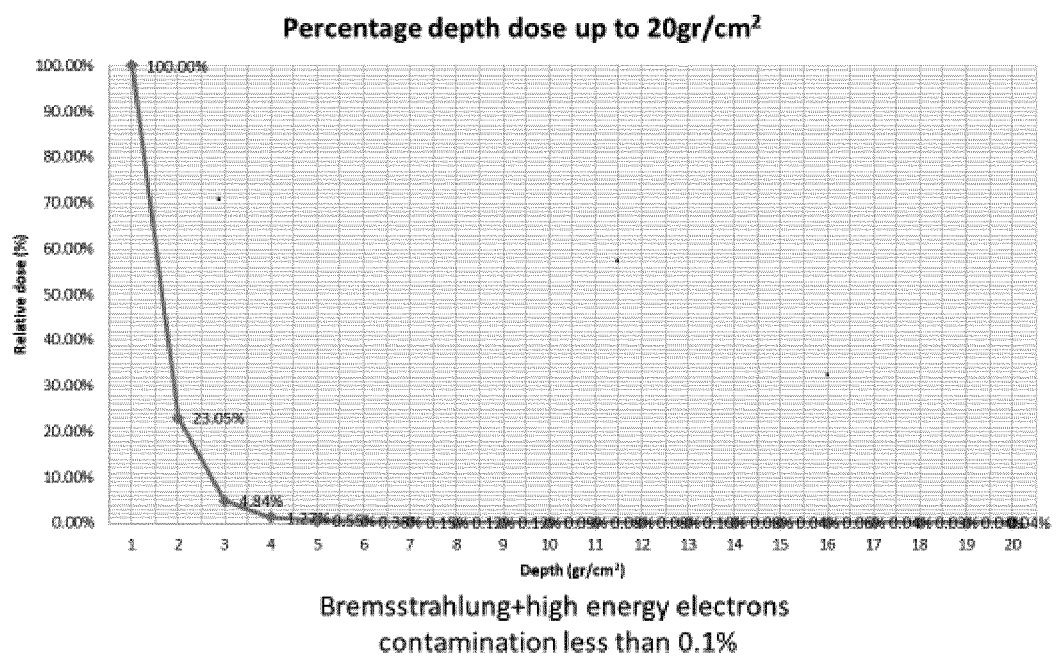
FIG. 6 a graph of the variation of % dose of the charged particles of the radiation beam with depth into the subject obtainable using the medical system of FIG. 3.
Figure 7:
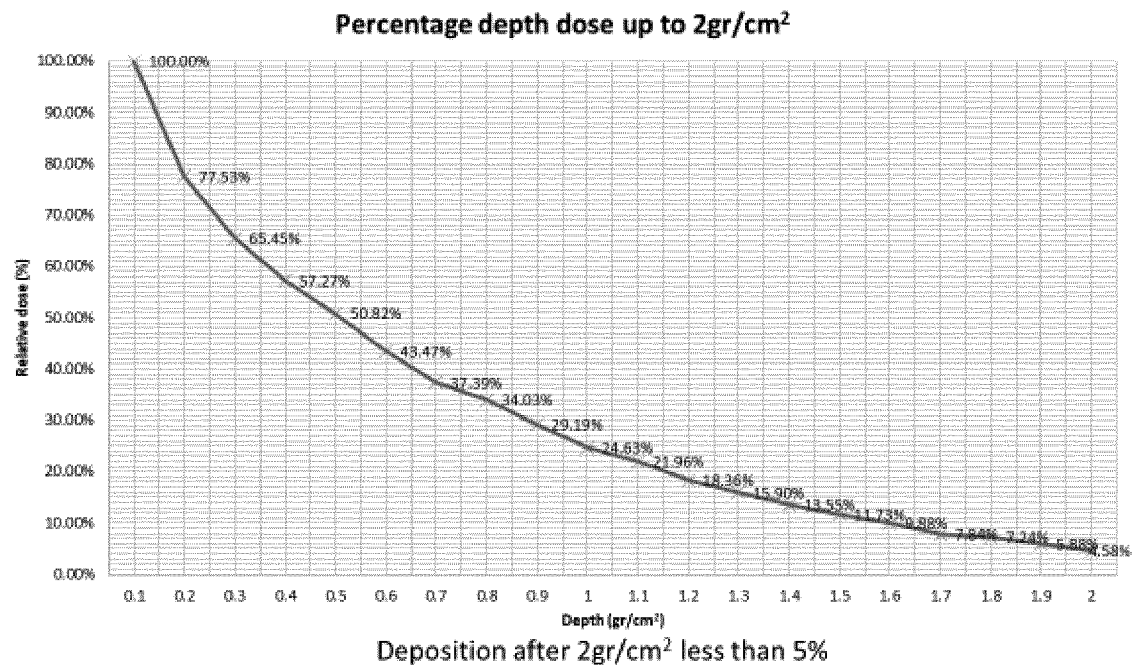
FIG. 7 a graph of another variation of the % dose of the charged particles of the radiation beam with depth in the subject obtainable using the medical system of FIG. 3.

FIG. 6 shows a variation of relative dose (%) with depth into the subject 210 achievable using the medical system 200 of FIG. 3 in which wakefield acceleration is used and suitably configured to create a radiation beam 215, 60 of charged particles having a broadband exponential or power law energy distribution. It can be seen in this dose-depth distribution that over 75% of the dose is delivered within 2 $g \cdot cm^{-2}$. Another distribution of relative dose (%) with depth into the subject 210 is shown in FIG. 7. It will be appreciated that the medical system 200 of FIG. 3 allows the energy distribution of the charged particles 40 in the radiation beam 215, 60 to be selected or dynamically adjusted to produce a required dose-depth profile, e.g. by adjusting the parameters of the beam source 10 and/or the particle source 35, by the use of a selection collimator 50 with a beam of charged particles 40 having a broadband energy spectrum to select portions (subsets) of the energy spectrum, by use of focusing optics such as magnets or plasma lenses and/or the like. In the example of FIG. 7, less than 5% of the dose is beyond 2 $g \cdot cm^{-2}$.

Figure 8:
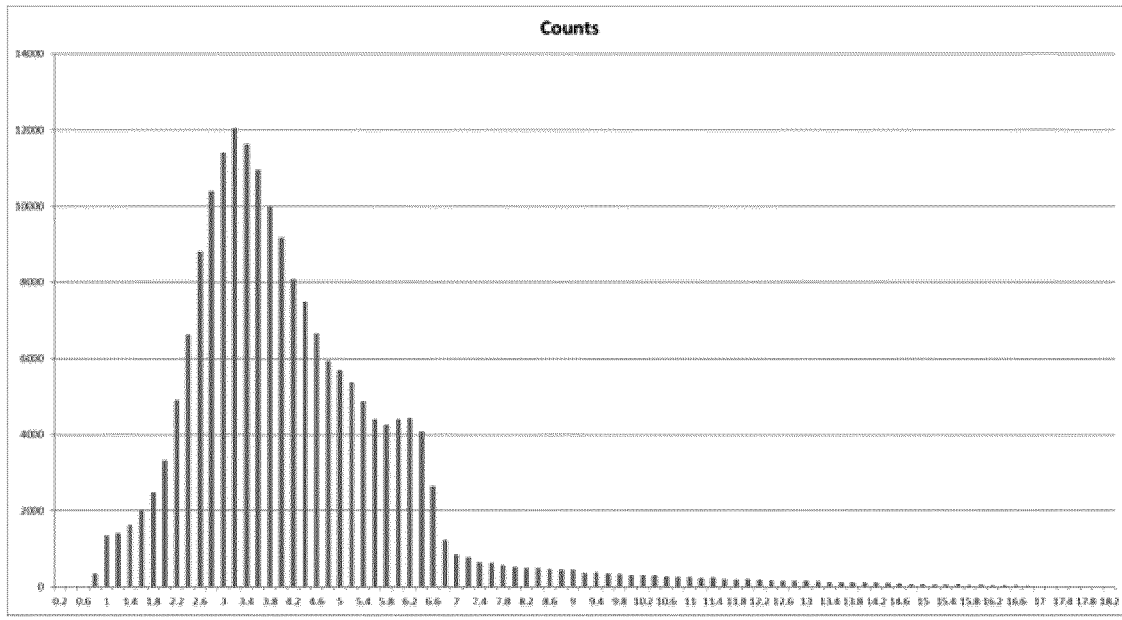
FIG. 8 a schematic showing a spectrum of the number of particles (y axis) versus their energy (x axis in MeV) obtainable using the medical system of FIG. 3.

FIG. 8 shows the results of a simulation and represents the number of particles (y axis) versus their energy (x axis in MeV) as an example of a broadband energy spectrum that can be obtained using the apparatus of FIG. 3.

Preferred embodiments described above comprise a laser pulse driven system that is used to generate electrons having a broadband energy distribution (e.g. in which the number or flux of charged particles in the radiation beam decreases with increasing energy, e.g. may decrease exponentially or according to a power law, over at least part or all of the energy range of the charged particles). The laser pulse is guided by a series of mirrors, optical fibres or fibre lasers, to the gas/plasma source and/or zone directly in front of the patient. This excitation laser pulse beamline has advantages relative to an electron excitation beam. For example, the mirrors which can be used to guide the laser pulse (or the fibres which go around corners) are much more lightweight than a magnet-based beamline for a charged electron beam. Also, an electron beamline with magnets etc. leads to Bremsstrahlung radiation when the electron beam is bent around corners, which makes the whole beamline emit radiation and requires radiation protection. If the laser pulse is guided with mirrors/fibres, no unhealthy radiation is produced, so there is no need for radiation protection. Therefore the whole beamline is very light and compact in comparison.

In addition, a broadband electron beam, in particular a low energy broadband electron beam, cannot be transported. This means that a broadband, low energy (1 keV to a few MeV) electron energy spectrum cannot be provided from a remote electron beam source to the skin tumour. Using a laser beam to provide a plasma wave or wakefield in the gas jet/plasma in from of the skin, however, can be used to produce these low energy electrons, which then hit the surface tumour and destroy it without damaging surrounding tissue, because they do not penetrate deeper.

It will be appreciated that the embodiments of the present disclosure herebefore described are given by way of example only and are not meant to limit the scope of thereof in any way.

It will be appreciated that embodiments of the present disclosure provide benefits over the prior art.

The invention claimed is:

1. A medical system for providing radiotherapy, the system comprising a particle accelerator configured to produce a radiation beam for irradiating at least a part of a subject, the particle accelerator comprising:
   a plasma zone comprising or configured to receive a plasma; and
   at least one beam source configured to provide an excitation beam through the plasma zone; wherein
      the medical system is configured to provide a plurality of charged particles in the plasma in a region that propagates through the plasma zone behind the excitation beam such that the plurality of charged particles are accelerated and usable to produce the radiation beam with a broadband energy distribution, wherein at least one of:
         at least part or all of the energy distribution of the radiation beam is exponential or power-law;
         particle accelerator is configured such that the radiation beam provides a dose-depth profile in which 75% or more of a dose of the radiation beam is delivered at and below 2 g/cm$^{-2}$; and
         particle accelerator is configured such that the radiation beam has an energy or energy distribution in a range from 10 eV to 10 MeV.

2. The system of claim 1 comprising an energy distribution control system for at least one of: selecting and adjusting the dose-depth profile or energy distribution of the radiation beam.

3. The system of claim 2, wherein the energy distribution control system comprises a controller configured to control the beam source to select or vary at least one parameter of the excitation beam to at least one of: select and adjust the dose-depth dose depth profile or energy distribution of the radiation beam.

4. The system of claim 3, wherein the at least one parameter of the excitation beam comprises one or more of: energy, duration, focus, beam size, beam wavelength, beam shape, and beam power density.

5. The system of claim 2, wherein the energy distribution control system comprises a selection collimator configured to select one or more of: a portion of the radiation beam and a portion of the charged particles to thereby select one or more of: the dose-depth profile and energy or energy distribution or dose-depth profile of the radiation beam.

6. The system of claim 2, wherein the energy distribution control system comprises a focusing system configured to focus the radiation beam to vary or select the charged particles that are incident on the subject from the plurality of charged particles dependent on the energy of the charged particles.

7. The system of claim 1, wherein the plurality of charged particles comprises electrons.

8. The system of claim 1, wherein the particle accelerator is, or comprises, a Wakefield Accelerator, such as a plasma wakefield accelerator (PWFA) or laser wakefield accelerator (LWFA).

9. The system of claim 1, comprising a gas jet configured to provide a plasma or gas from which the plasma is formed into the plasma zone.

10. The system of claim 1, wherein the particle accelerator comprises a target material and a first laser configured to focus a first laser beam onto the target material, and wherein at least one parameter of the target material is selected or varied to determine characteristics of the radiation beam and the at least one parameter of the target material comprises at least one of: physical state, thickness, density, material, composition, structure, temperature and shape.

11. The system of claim 10, wherein one or more of: the first laser and the beam source is configured to operate in a pulsed mode at between 1 Hz and 1 MHz.

12. The system of claim 1, wherein the beam source is a laser and the laser is a fibre laser.

13. The system of claim 1, wherein the radiation beam has an energy distribution that is exponential or power-law over the range of 10 eV to 10 MeV.

14. The system of claim 1 comprising targeting means for targeting the radiation beam produced by the particle accelerator onto the subject with at least one of: a selectable focus and a selectable angle of incidence.

15. A method of treating a skin condition of a subject, the method comprising:
   using the medical system of claim 1 to produce a radiation beam comprising the plurality of charged particles with a broadband energy distribution; and
   irradiating a subject with the radiation beam.

16. The method of claim 15, wherein at least one of:
   the broadband energy distribution is exponential or power-law;
   the method comprises using the medical system to deliver 75% or more of a dose of the charged particles at and below 2 g/cm$^{-2}$;
   and
   the method comprises using the medical system to deliver the radiation beam with an energy or energy distribution in a range from 10 eV to 10 MeV.

17. The method of claim 15, comprising providing the radiation beam at an angle of incidence to a normal of a surface of the subject of 0 degrees.

18. The method of claim 15, wherein the skin condition comprises a tumour.

19. A method of adapting a medical radiotherapy apparatus comprising a LINAC to produce a broadband radiation beam having an energy distribution that is exponential or power-law, the method comprising fitting the apparatus with a gas jet or plasma cell for providing a plasma zone, the gas jet or plasma zone being arranged such that a plurality of charged particles are receivable in the plasma zone in a region that propagates through the plasma zone behind an excitation beam such that the plurality of charged particles are accelerated and usable to produce the radiation beam with a broadband energy distribution, wherein at least one of:

- at least part or all of the energy distribution of the radiation beam is exponential or power-law;
- the radiation beam delivers 75% or more of a dose of the charged particles at and below 2 $g/cm^{-2}$; and
- the radiation beam has an energy or energy distribution in a range from 10 eV to 10 MeV.

20. The method of claim 19, wherein a particle beam output of the LINAC is directed into or through the gas jet or plasma cell to facilitate wakefield acceleration.

* * * * *